United States Patent
Wang

(10) Patent No.: US 11,406,346 B2
(45) Date of Patent: Aug. 9, 2022

(54) SURGICAL POSITION CALIBRATION METHOD

(71) Applicant: TAIWAN MAIN ORTHOPAEDIC BIOTECHNOLOGY CO., LTD., Taichung (TW)

(72) Inventor: Min-Liang Wang, Taichung (TW)

(73) Assignee: TAIWAN MAIN ORTHOPAEDIC BIOTECHNOLOGY CO., LTD., Taichung (TW)

(*) Notice: Subject to any disclaimer, the term of this patent is extended or adjusted under 35 U.S.C. 154(b) by 951 days.

(21) Appl. No.: 16/148,938

(22) Filed: Oct. 1, 2018

(65) Prior Publication Data

US 2020/0100756 A1    Apr. 2, 2020

(51) Int. Cl.
| | |
|---|---|
| G06T 7/70 | (2017.01) |
| G06T 7/55 | (2017.01) |
| A61B 34/20 | (2016.01) |
| A61B 6/00 | (2006.01) |
| G06T 19/00 | (2011.01) |
| A61B 90/00 | (2016.01) |
| G02B 27/01 | (2006.01) |

(52) U.S. Cl.
CPC ............ *A61B 6/584* (2013.01); *A61B 6/4441* (2013.01); *A61B 34/20* (2016.02); *G06T 7/55* (2017.01); *G06T 7/70* (2017.01); *G06T 19/006* (2013.01); *A61B 2034/2065* (2016.02); *A61B 2090/365* (2016.02); *A61B 2090/374* (2016.02); *A61B 2090/3762* (2016.02); *G02B 27/0172* (2013.01); *G02B 2027/014* (2013.01); *G02B 2027/0141* (2013.01); *G06T 2207/10081* (2013.01); *G06T 2207/10088* (2013.01); *G06T 2207/10116* (2013.01); *G06T 2207/20221* (2013.01)

(58) Field of Classification Search
CPC ....... A61B 6/584; A61B 34/20; A61B 6/4441; A61B 2034/2065; A61B 2090/365; A61B 2090/3762; G06T 7/55; G06T 7/70; G06T 19/006; G02B 27/0172; G02B 2027/014
USPC ...................................................... 348/276
See application file for complete search history.

(56) References Cited

U.S. PATENT DOCUMENTS

2003/0130576 A1*  7/2003  Seeley ................. A61B 6/4441
                                              600/426
2003/0181809 A1*  9/2003  Hall ....................... A61B 6/463
                                              600/425

(Continued)

*Primary Examiner* — Hai Tao Sun
(74) *Attorney, Agent, or Firm* — Pai Patent & Trademark Law Firm; Chao-Chang David Pai

(57) ABSTRACT

A surgical position calibration method for getting the augmented and mixed reality of a surgical instrument includes the following steps: placing a calibration plate under a C-ARM to take C-ARM images, with the calibration plate provided with geometric patterns; inputting the C-ARM images into a computer to make 2D image maps; finding the center point of each geometric pattern on the calibration plate; defining a first reference calibration point; finding the distance between the center point of each other geometric pattern and the first reference calibration point to set up a translation matrix formula to form a 3D space image map; placing a surgical instrument at any position above the calibration plate; using the translation matrix formula generating a spatial variation image for the displacement of the surgical instrument; and forming a new spatial variation image.

10 Claims, 3 Drawing Sheets

(56) References Cited

U.S. PATENT DOCUMENTS

2014/0221824 A1* 8/2014 Rai .................. A61B 90/39
  600/424
2017/0202633 A1* 7/2017 Liu .................. A61B 90/37
2018/0193098 A1* 7/2018 Caluser ............. A61B 34/20

* cited by examiner

SURGICAL POSITION CALIBRATION METHOD

BACKGROUND OF THE INVENTION

1. Field of the Invention

The present invention relates to a surgical position calibration method, and more particularly to a surgical position calibration method that can rapidly establish augmented and mixed reality of a surgical instrument.

2. Description of the Related Art

In recent years, with the development of new health care technology, computer-assisted surgery has increased significantly. Since the accuracy of surgical instruments and imaging technology has improved, doctors not only can enhance the quality of their surgery, but also can minimize patient wounds. Generally, a computer-assisted surgery consists of four parts: acquiring images from a patient, image analysis and processing, pre-diagnosis and surgical planning simulation, and finally receiving the surgery guidance for the patient. Computer-assisted surgery of the surgery currently is divided into the following steps: first, using tomography images, including computerized tomography (CT), magnetic resonance imaging (MRI), X ray, nuclear medicine imaging, reconstructed 3D models (non-real-time image), and second: using the mobile C-arm X-ray machine or ultrasound imaging in the operating room as an auxiliary guide (real-time image) and a non-image-based guidance system.

Clinical application of image guided surgical systems, including spinal surgery guide (e.g., pedicle screw fixation, removal of damaged sites, removal of lumps, and disposing electrode to a fixed depth for epilepsy patients); head lesion surgery (e.g., treatment of meningioma, craniopharyngioma, chondrosarcoma, and other lesions in the cranial portion); tumor resection tissue sections; treatment of Parkinson's disease; treatment of huibu brain stereotaxic of psychiatric disorders; audition functional sinus surgery; neurovascular surgical repair and ventricular bypass surgery and ventricular shunt replacement surgery. This system can also be used for the hip and knee surgery, such as total knee arthroplasty, total hip replacement surgery, and anterior cruciate ligament reconstruction.

Operation must be combined with image guide, electronic, machinery, and other techniques, so the orientation of the surgical instrument projected onto the image may assist a physician to grasp the relative orientation between the device and the patient and to achieve the purpose of navigation. Before the operation, the doctor first puts a mark on the patient's surgical position, and then allows the patient to undergo a computerized tomography or magnetic resonance imaging examination. The image of computerized tomography or magnetic resonance image is reconstructed in the computer to form the three-dimensional position near the surgical site, and the location of the anomaly and normal functional area are indicated. At the time of surgery, surgical site of the patient and the surgical instruments have mounting marks, and then infrared camera (ultrasound or the like) can label the localization and relative positions of the surgical site and the surgical instrument simultaneous to create space surgery relationship according to these infrared signals reflected from the mark. In addition, the surgeon may use the head or heads-up display through the eyepiece to see the image reorganization.

Augmented Reality (Augmented Reality, AR) and Mixed Reality (Mixed Reality, MR) are generally used to display virtual information on the real image of the patient. Particularly in minimally invasive surgery using the endoscope in the past, the overlay of images is performed in the augmented and mixed reality images. This way can not be directly observed by the camera, but now the image can be seen prior to surgery. Augmented and mixed reality assist the surgeon to see through the patient's body part, so that the doctor prior to the surgical site visits, vital structures thereof can be effectively positioned without confirming the position beforehand by performing the operation. Augmented and mixed reality technology seems to be currently the most promising research, which helps guide the surgeon and process supervision robotic surgery. However, it shall require a precious surgical position calibration method to rapidly establish augmented and mixed reality of a surgical instrument first.

In view of the above problems, it is necessary to provide a surgical position calibration method that can rapidly establish augmented and mixed reality of a surgical instrument for the application of augmented and mixed reality computer assisted glasses for surgical operation.

BRIEF SUMMARY OF THE INVENTION

An object of the present invention is to provide a surgical position calibration method for use in surgery, to solve the problem of the position relationship between the aforementioned surgical instrument and the surgical site of the patient.

A surgical position calibration method, comprising the following steps:
- Step 1: placing a calibration plate under a C-ARM machine to take a plurality of C-ARM images, the calibration plate provided with a plurality of geometric patterns;
- Step 2: inputting the C-ARM images into a computer to make a plurality of 2D image maps;
- Step 3: finding the center point of each geometric pattern on the calibration plate in the 2D image maps;
- Step 4: defining the center point of one of the geometric patterns on the calibration plate in one of the 2D image maps as a first reference calibration point;
- Step 5: by using the first reference calibration point as a positioning reference point, finding the distance between the center point of each of the other geometric patterns on the calibration plate and the first reference calibration point to set up a translation matrix formula to form a 3D space image map;
- Step 6: placing a surgical instrument to be used at any position above the calibration plate to define a second reference calibration point;
- Step 7: by using the translation matrix formula, generating a spatial variation image for the displacement of the surgical instrument:
- Step 8: inputting the spatial variation image to the computer, and combining the spatial variation image with the image of the surgical site to be used in other surgical procedures as a new spatial variation image.

According to one aspect of the present invention, the geometric patterns are the same repeated geometric patterns.

According to one aspect of the present invention, the distances of the geometric patterns are arranged in an equal ratio.

According to one aspect of the present invention, in Step one: the plurality of C-ARM images taken includes at least 10 C-ARM images.

According to one aspect of the present invention, in Step 5, the translation matrix formula is obtained from the positional characteristics of the center point of each geometric pattern detected by a function library and then performed by a mathematical operation.

According to one aspect of the present invention, for obtaining the 3D space image map, the 3D structural patterns of the 3D space image are used to generate a 3D virtual space and thus the 3D real positions of each features are used for 3D positioning of the 3D space image.

According to one aspect of the present invention, the function library is a 3D computer vision library written in C/C++ language.

According to one aspect of the present invention, in Step 8: the surgical site image required to be used in other surgical procedures is selected from one of the following: computer tomography imaging (CT), magnetic resonance imaging (MRI), X-ray imaging, positive medical imaging and nuclear medical imaging.

According to one aspect of the present invention, in Step 8: the spatial variation image is combined with the image of the surgical site using an image overlay software.

According to one aspect of the present invention, the new spatial variation image is inputted into a surgical eyeglass worn by a surgeon.

DETAILED DESCRIPTION OF THE INVENTION

While the present invention can be applied in different forms of embodiment, the drawings and the following description are merely of preferred embodiments of the present invention by way of examples, and are not intended to limit the invention to the illustrated and/or described in a particular embodiment.

The present invention provides a surgical position calibration method that can be applied to computer-assisted glasses with enhanced authenticity for surgery (namely, augmented and mixed reality computer assisted glasses for surgical operation). The enhanced authenticity can be seen as a mixture of virtual and real-world space that synchronizes patient information.

Figure 1:
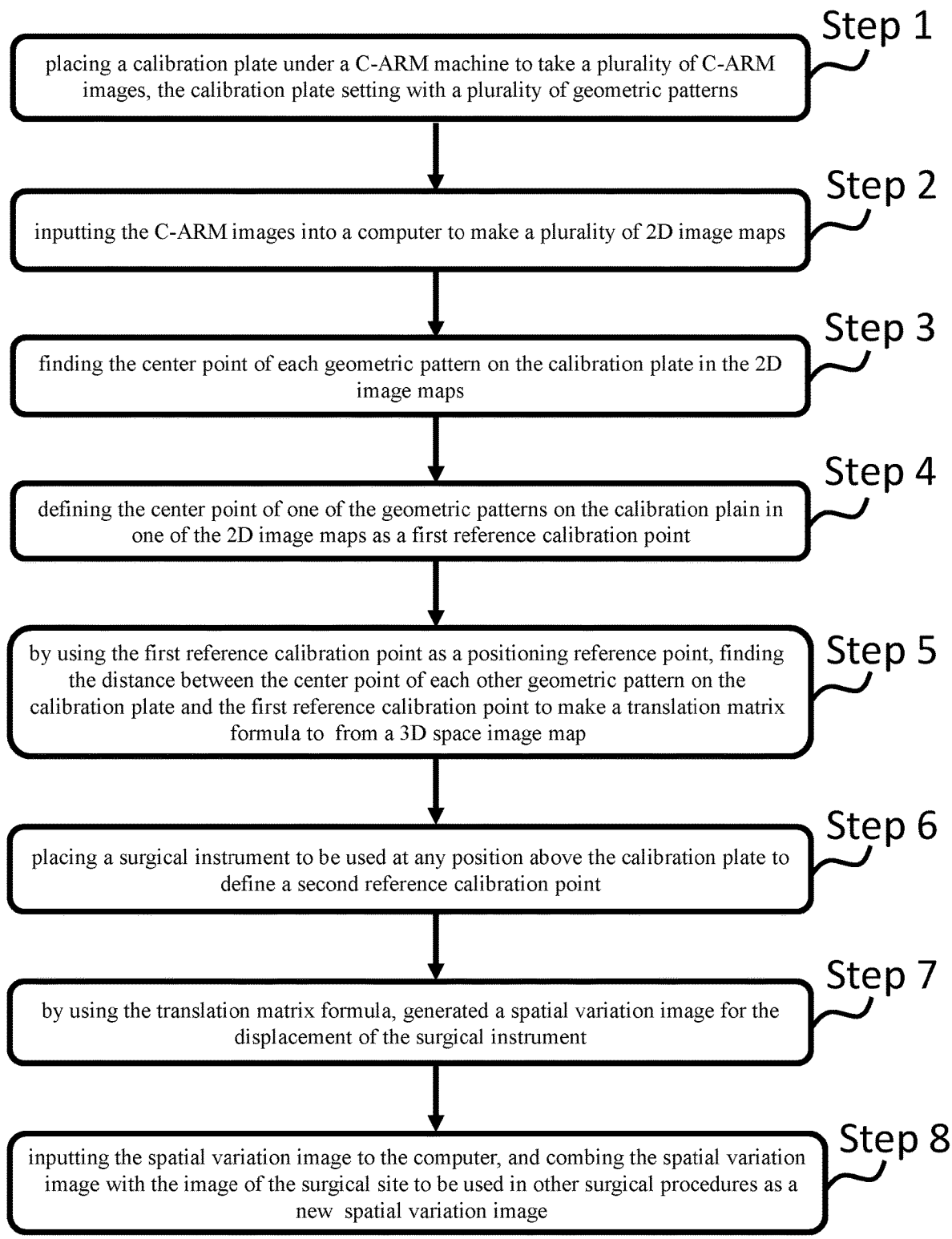
FIG. 1 is a procedure flowchart of the surgical position calibration method of the present invention.
Figure 2A:
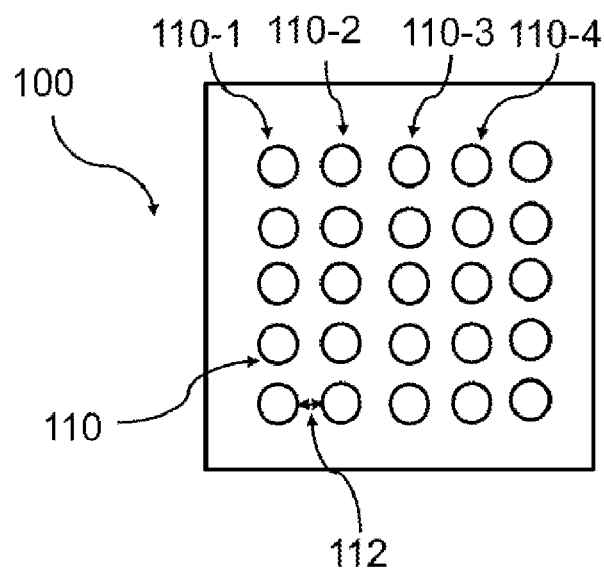
FIG. 2A is a schematic diagram of a plurality of geometric patterns using circular patterns on the calibration plate.
Figure 2B:
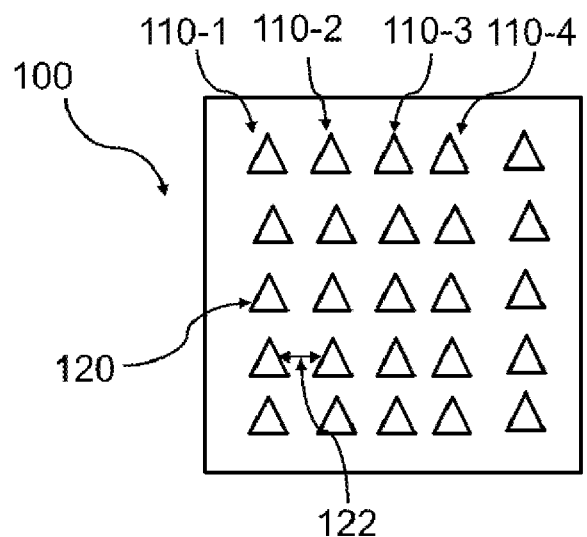
FIG. 2B is a schematic diagram of a plurality of geometric patterns using triangular patterns on the calibration plate.
Figure 3:
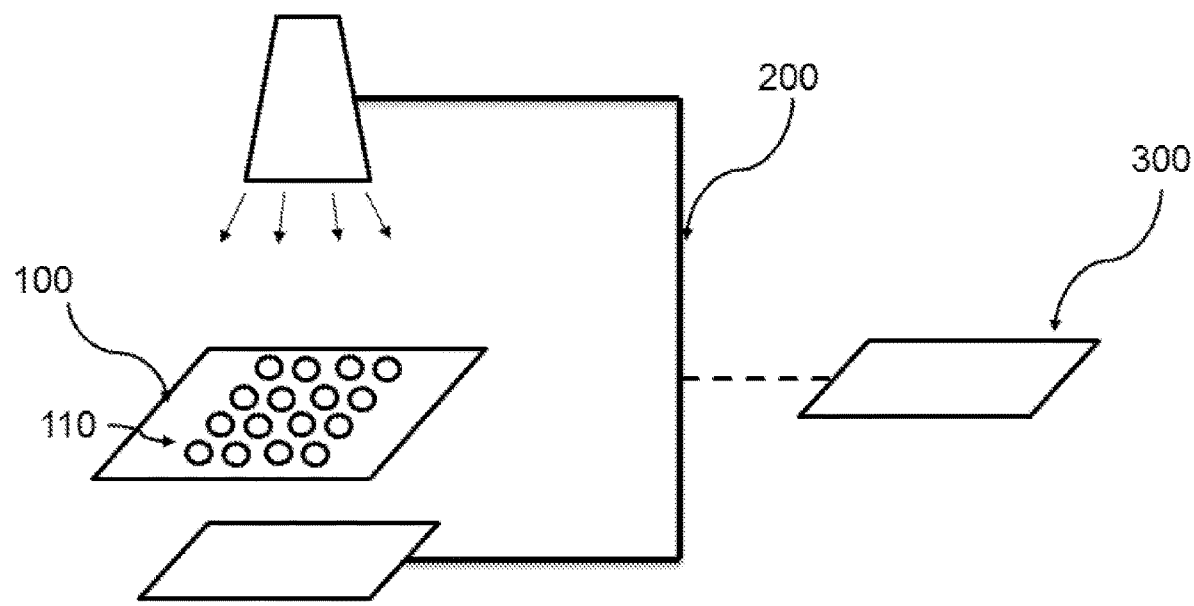
FIG. 3 is a schematic diagram of a calibration plate being placed under a C-ARM to take a plurality of C-ARM images.

FIG. 1 shows a procedure flowchart of the surgical position calibration method of the present invention. FIG. 2A is a schematic diagram of a plurality of geometric patterns using circular patterns on the calibration plate, and FIG. 2B is a schematic diagram of a plurality of geometric patterns using triangular patterns on the calibration plate, and FIG. 3 is a schematic diagram showing a calibration plate being placed under a C-ARM to take a plurality of C-ARM images. The surgical position calibration method of the present invention comprises the following steps:

Step 1: placing a calibration plate 100 under a C-ARM machine 200 to take a plurality of C-ARM images, with the calibration plate 100 provided with a plurality of geometric patterns 110, 120;

Step 2: inputting the C-ARM images into a computer 300 to make a plurality of 2D image maps;

Step 3: finding the center point of each geometric pattern on the calibration plate in the 2D image maps;

Step 4: defining the center point of one of the geometric patterns on the calibration plate in one of the 2D image maps as a first reference calibration point;

Step 5: by using the first reference calibration point as a positioning reference point, finding the distance between the center point of each other geometric pattern on the calibration plate and the first reference calibration point to set up a translation matrix formula to form a 3D space image map;

Step 6: placing a surgical instrument to be used at any position above the calibration plate to define a second reference calibration point;

Step 7: by using the translation matrix formula, generating a spatial variation image for the displacement of the surgical instrument;

Step 8: inputting the spatial variation image to the computer 300, and combining the spatial variation image with the image of the surgical site to be used in other surgical procedures as a new spatial variation image.

In an embodiment, the geometric patterns can be formed on the calibration plate by, for example, drawing or depositing some color. The geometric patterns are the same repeated geometric patterns, namely, the same repeated pattern. The geometric patterns are selected from, but not limited to, circular patterns or triangular patterns, as shown in FIG. 2A and FIG. 2B, respectively. In a preferred embodiment, the geometric patterns are selected from circular patterns.

The distance of the geometric patterns is defined as the distance between the centers of the two immediately adjacent geometric patterns. In an embodiment, a distance ratio of the geometric patterns is set as an equal value. For example, the distances between the first geometric pattern 110-1 and second geometric pattern 110-2 is 0.1 mm, the distances between the second geometric pattern 110-2 and third geometric pattern 110-3 is 0.2 mm, and the distances between the third geometric pattern 110-3 and fourth geometric pattern 110-4 is 0.4 mm. Namely, the distance ratio is equal to 2. As shown in FIG. 2A and FIG. 2B, the geometric patterns have a distance 112, 122 between 0.1 mm and 1 mm. In a preferred embodiment, the geometric patterns have a distance between 0.2 mm and 0.5 mm to have precious calibration.

In an embodiment, in Step 1: the plurality of C-ARM images taken includes at least 50 C-ARM images. In a preferred embodiment, the plurality of C-ARM images taken includes 50 to 100 C-ARM images. And, the plurality of C-ARM images are taken with a varying distance between a C-ARM camera and the calibration plate.

In an embodiment, in Step 5, the translation matrix formula is obtained from the positional information of the center point of each geometric pattern detected by a function library and then performed by a mathematical operation.

The translation matrix formula is from a three-dimensional model of the component library constructed. The function library is then constructed by a texture component and 3D image rendering core, to construct the bounding box using the three-dimensional model component library; to implement collision detection; to calculate component libraries, to implement force feedback and serial communication using the data communication component library function console such as 802.11g, TCP/IP or RS232, etc. In an embodiment, the function library is a 3D computer vision library written in C/C++ language.

For obtaining the 3D space image map, 3D structural patterns of the 3D space image are used to generate a 3D virtual space. The plurality of C-ARM images are integrated to form a 3D space image, and the 3D real position information in the 3D space image are used for 3D positioning the 3D structural patterns of the 3D space image, thus to obtain the 3D space image map. Here, the 3D real position information means that the 3D real positions of the center point of each geometric pattern on the calibration plate and the 3D real positions of the surgical instrument to be used at any position above the calibration plate.

In an embodiment, in Step 7: by using the translation matrix formula, a spatial variation image is generated for the displacement of the surgical instrument.

In an embodiment, in Step 8: the surgical site image required to be used in other surgical procedures is obtained by an imaging method selected from one of the following: computer tomography imaging (CT), magnetic resonance imaging (MRI), X-ray imaging, positive medical imaging and nuclear medical imaging.

In an embodiment, in Step 8: the spatial variation image are combined with the image of the surgical site to be used in other surgical procedures using an image overlay software.

The computer 300 operates the image overlay software for processing images and data, and for communicating images and data via wired or wireless connections. For example, the image overlay software can be used by the medical clinician to manipulate, convert, and overlay images collected by the surgical site image required to be used in other surgical procedures. Although different machines may produce images in different formats, it is desirable that the image overlay software be capable of converting one or more image formats into another one or more different formats, so that the images collected by different devices can be displayed together in an overlying fashion. Thus, the image overlay software is configured to access, display, convert, and manipulate a new spatial variation image by combining the spatial variation image with the image of the surgical site to be used in other surgical procedures in various formats including, for example, DICOM images, CAD images, STL images, or the like. The image overlay software permits a clinician to review digital images, visualize virtual models and create images overlays on a display of the surgical eyeglass worn by a surgeon.

In Step 8: in addition, the image overlay software may be operable to create and transmit laboratory prescriptions, such as digital models of anatomical features, to an on-site or off-site laboratory for use in fabricating a prosthetic (e.g., partial dentures, implant abutments, orthodontic appliances, and the like), surgical guides, or the like. Images overlay software such as OOOPDS 3D medical software is capable of superimposing or overlaying images.

In an embodiment, the new spatial variation image is inputted into a surgical eyeglass worn by a surgeon. The surgeon, by means of the surgical eyeglass, defines an operation depth for the entire optical system on the surgical eyeglass and, by moving his head, automatically, illuminates the operating area by pointing the headlight according to head movement. Thus the image which is returned from the surgical site is always directed along the same line as illuminating the operating area. The surgeon, by moving his head, automatically aims the headlight, and the eyes of the surgeon perceives the area illuminated by the beam which then, based on the orientation of the optical system on the surgical eyeglass, produces an image which essentially is completely indicative of exactly what the surgeon is seeing, at the same magnification.

According to the invention disclosed, the present invention provides a surgical position calibration method that can rapidly establish an augmented and mixed reality of a surgical instrument for the application of augmented and mixed reality computer assisted glasses for surgical operation. It has the following advantages including reducing operation time, reducing the amount of X-ray radiation, and assisting positioning operation.

While the invention has been disclosed in the foregoing preferred embodiments, they are not intended to limit the present invention, and one skilled in the art, without departing from the spirit and scope of the present disclosure, may make various changes or modifications. Therefore the scope of the present invention is best defined by the appended claims.

What is claim is:

1. A surgical position calibration method, comprising the following steps:
   Step 1: placing a calibration plate under a C-ARM machine to take a plurality of C-ARM images, the calibration plate provided with a plurality of geometric patterns;
   Step 2: inputting the C-ARM images into a computer to make a plurality of 2D image maps;
   Step 3: finding the center point of each geometric pattern on the calibration plate in the 2D image maps;
   Step 4: defining the center point of one of the geometric patterns on the calibration plate in one of the 2D image maps as a first reference calibration point;
   Step 5: by using the first reference calibration point as a positioning reference point, finding the distance between the center point of each other geometric pattern on the calibration plate and the first reference calibration point to make a translation matrix formula to form a 3D space image map;
   Step 6: placing a surgical instrument at any position above the calibration plate to define a second reference calibration point;
   Step 7: using the translation matrix formula to generate a spatial variation image for the displacement of the surgical instrument;
   Step 8: inputting the spatial variation image to the computer, and combining the spatial variation image with the image of the surgical site to be used in other surgical procedures as a new spatial variation image, and then inputting the new spatial variation image into a surgical eyeglass worn by a surgeon,
   wherein the plurality of geometric patterns provided on the calibration plate are arranged in multiple rows, and distance ratios between these adjacent geometric patterns are the same, and the same distance ratios between these adjacent geometric patterns will be greater than 1 so that the distances between the plurality of geometric patterns in each row are arranged from narrow to wide.

2. The surgical position calibration method according to claim 1, wherein the geometric patterns are the same repeated geometric patterns.

3. The surgical position calibration method according to claim 1, wherein the geometric patterns are circular or triangular patterns.

4. The surgical position calibration method according to claim 1, wherein the geometric patterns are the same repeated geometric patterns.

5. The surgical position calibration method according to claim 1, wherein in Step 1: the plurality of C-ARM images taken includes at least 10 C-ARM images.

6. The surgical position calibration method according to claim 1, wherein in Step 5, the translation matrix formula is obtained from positional information of the center point of each geometric pattern detected by a function library and then performed by a mathematical operation.

7. The surgical position calibration method according to claim 1, wherein for obtaining the 3D space image map, 3D structural patterns of the 3D space image are used to generate a 3D virtual space.

8. The surgical position calibration method according to claim 6, wherein the function library is a 3D computer vision library written in C/C++ language.

9. The surgical position calibration method according to claim 1, wherein in Step 8: the image of the surgical site to be used in other surgical procedures is obtained by an imaging method selected from one of the following: computer tomography imaging (CT), magnetic resonance imaging (MRI), X-ray imaging, positive medical imaging and nuclear medical imaging.

10. The surgical position calibration method according to claim 1, wherein in Step 8: the spatial variation image is combined with the image of the surgical site to be used in other surgical procedures by using an image overlay software.

* * * * *